(12) United States Patent
Yagi

(10) Patent No.: US 6,359,962 B1
(45) Date of Patent: Mar. 19, 2002

(54) FLOURESCENT X-RAY ANALYZER

(75) Inventor: Shigeki Yagi, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/590,200

(22) Filed: Jun. 8, 2000

(51) Int. Cl.⁷ .......................................... G01N 23/223
(52) U.S. Cl. .......................................... 378/44; 378/45
(58) Field of Search .................................. 378/44–50

(56) References Cited

U.S. PATENT DOCUMENTS 5,892,809 A * 4/1999 Wittry ........................ 378/45

* cited by examiner

*Primary Examiner*—Craig E. Church
(74) *Attorney, Agent, or Firm*—Adams & Wilks

(57) ABSTRACT

A fluorescent X-ray analyzer has an X-ray generating device for generating X-rays, a shutter for shielding an X-ray flux generated from the X-ray generating device from radiating to a sample to be measured, and a shutter drive mechanism for opening and closing the shutter. An X-ray detecting device detects secondary X-rays generated when the X-ray flux is radiated to the sample to be measured. A measurement start order device orders the start of a measurement. An image input device optically reads and obtains image data corresponding to an external appearance and a background of the sample to be measured. A first storage circuit stores image data obtained by the image input device. A second storage circuit stores data related to a figure previously registered. A data comparing device compares the image data stored in the first storage circuit with the data stored in the second storage circuit. A state detecting device detects an installation state of the fluorescent X-ray analyzer.

12 Claims, 4 Drawing Sheets

FLOURESCENT X-RAY ANALYZER

BACKGROUND OF THE INVENTION

Field of the Invention

The present invention relates to a portable fluorescent X-ray analyzer used for a purpose of outdoor elementary analysis to be conducted in archaeological material search, criminal site investigation or fire initial investigation.

With a usual fluorescent X-ray analyzer, an object to be measured is contained within a sealed cover type sample chamber structure. Prevention against X-ray leaks to the outside of the apparatus is realized comparatively easily and reliably by such methods as checking the state of the sample chamber door. In the case of a portable fluorescent X-ray analyzer for frequent use at an unspecified, typically outdoor site on the other hand, X-ray radiation is completely open in the direction of the object to be measured. Consequently, in order to secure safety for the measurer or other persons that are around the fluorescent X-ray analyzer, it has been requisite for the measurer to pay careful attention to realize installation conditions which avoid exposure to X-rays. Usually when X-ray radiation is carried out, reference is made to the state of a plurality of sensors or switches provided on the fluorescent X-ray analyzer in determining whether the specified conditions necessary for the shutter to be safely opened are met. For example, the apparatus is structured so that the X-ray radiation is started only when the shutter operation release switch is turned on and also the lead switch is turned on by the contact of the lever of the lead switch mounted in the area beyond the X-ray radiation port of the fluorescent X-ray analyzer with one part of the sample to be measured. In order to maintain such a condition, a method has been adopted that a measuring head of the fluorescent X-ray analyzer is fixed to a precise position using a fixture such as a tripod. Further, safety is secured by obeying a procedure that the shutter operation release switch is turned off before carrying the fluorescent X-ray analyzer to a measurement site, and the measurer turns on this switch only when preparation for measurement is completed.

There are often cases that there is difficulty in placing a fluorescent X-ray analyzer in contact with one part of a sample to be measured during fixation of the analyzer at a measurement site. There are cases where contact is impossible because of the size or property of the sample to be measured. However, in the absence of such a safety mechanism, there may be a case that the installation conditions of the fluorescent X-ray analyzer are changed due to a blast of strong wind or such, resulting in accidental X-ray radiation to other points than the sample to be measured. The realization of a state in which the safety mechanism operates through fixing the position of the fluorescent X-ray analyzer makes installation difficult, lessening mobility of the portable fluorescent X-ray analyzer. However, there is a dilemma that the possibility increases of causing an X-ray exposure accident unless a safety mechanism is provided to enable measurement only under certain specified conditions.

SUMMARY OF THE INVENTION

It is an object of the present invention to obtain a portable fluorescent X-ray analyzer which solves the above problems and is high in safety and easy to handle.

In order to achieve the above object, the present invention has, in a fluorescent x-ray analyzer, image input means for optically reading the external appearance and the background of the sample to be measured, first storage means for storing image data acquired by the image input means, second storage means for storing related data to a figure previously registered, data comparing means for comparing data stored in the first storage means with data stored in the second storage means, state detecting means for detecting the installation state of the fluorescent X-ray analyzer, and x-ray switch means to control the shutter drive means correspondingly to outputs of the data comparing means and the state detecting means when a measurement start instruction is given.

The image input means optically reads a sample to be measured and the background in the vicinity thereof. An object of a specific shape is put in the vicinity of the sample to be measured and read by the image input means. The image data read at this time is stored in the first storage means. On the other hand, the second storage means stores data related to the above specific shape. The data comparing means determines whether or not image data corresponding to the specific shape is contained in the image data of the first storage means, based on the data of the second storage means. If the data is included, an activation signal is outputted to the X-ray switch means. The state detecting means outputs an activation signal to the X-ray switch means when detecting that the fluorescent X-ray analyzer is installed in a safe state. When the measurement start instructing means instructs that measurement start, the X-ray switch means examines signals from the data comparing means and state detecting means and controls the shutter drive means to open a shutter only in the case both are activating signals.

DETAILED DESCRIPTION OF THE PREFERRED EMBODIMENT

The present invention will now be described by way of an embodiment with reference to the drawings.

Figure 1:
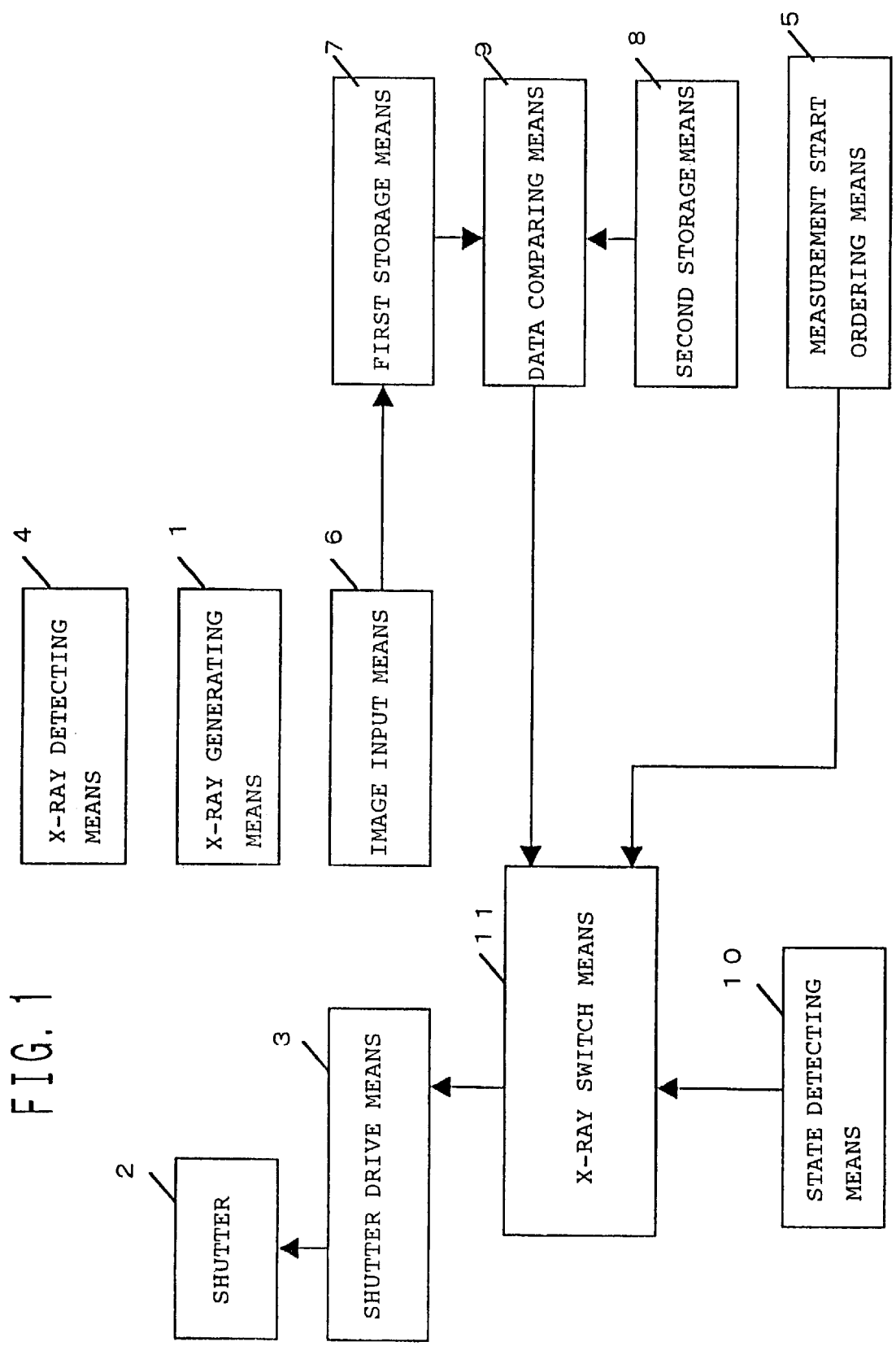
FIG. 1 is a function block diagram showing a typical configuration of a fluorescent X-ray analyzer of the present invention.
Figure 2:
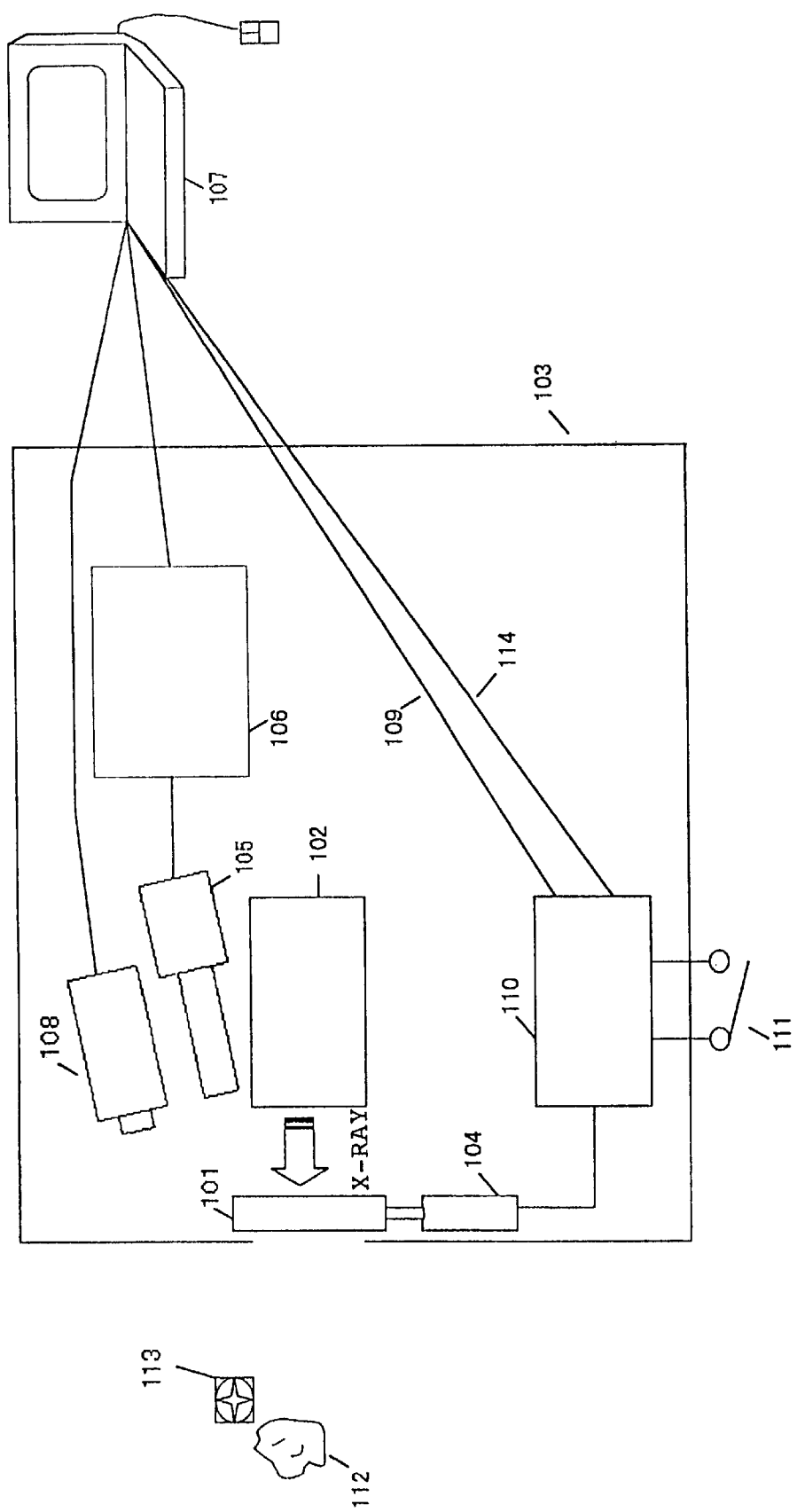
FIG. 2 is a block diagram of an embodiment of a fluorescent X-ray analyzer of the invention.

FIG. 1 is a functional block diagram showing a typical configuration of a fluorescent X-ray analyzer according to the present invention. FIG. 2 is a schematic view of an embodiment of the fluorescent X-ray analyzer of the invention. A shutter 101 of FIG. 2 corresponds to a shutter 2 of FIG. 1, which is made of a metal having a sufficient thickness for providing a complete X-ray shield. An X-ray generating source 102 of FIG. 2 corresponds to X-ray generating means 1 of FIG. 1, which adopts an end-window type small-sized X-ray bulb and realizes apparatus size reduction. The X-ray generating source 102 generates a flux of a fluorescent X-ray to be passed through an X-ray radiation window provided in a measuring head housing 103 of the fluorescent X-ray analyzer and radiated to a sample to be measured. However, when measurement is not being carried out, shielding is made by the shutter 101 so as not to leak X-rays to the outside of the measuring head. The shutter 101 is mechanically operated by an actuator 104, such as a solenoid. This actuator 104 corresponds to shutter drive means 3 of FIG. 1. The X-ray detecting means 4 of FIG. 1 corresponds to an X-ray detector 105, detecting circuit 106 and computer 107 in FIG. 2. The X-ray detector 105 detects secondary X-rays coming from the sample to be measured and converts them into electric pulses. The electric pulses are inputted to the detecting circuit 106 and the wave height of the electric pulses are measured, the result of which is sent to the computer 107 where an X-ray spectrum is generated that represents intensity vs. energy. The X-ray detector 105 can utilize a Si or Ge semiconductor detector, a scintillation detector or a proportional counter tube, in accordance with the purpose of use. The electric pulses inputted to the detecting circuit 106 are amplified to be turned later into a signal having a level that is easy to process. At this time, a waveform shaping process is also performed to secure a required count rate and obtain a preferred energy resolution. The electric pulse thus processed is converted in wave height into a digital value by an A/D converter. The secondary X-rays thus sequentially detected are represented as a spectrum in the format of count vs. wave height or energy. The counting process is realized by utilizing hardware such as MCA or a computer.

In order to radiate a primary X-ray to the part to be measured, it is necessary to accurately position the measuring head housing 103. An imaging apparatus 108 such as a CCD camera is provided on a measuring head housing 103 side to observe the sample to be measured. Thus the positional relationship of the sample to be measured and the measuring head housing 103 can be easily grasped and correctly adjusted for proper measurement. If an image signal is inputted from the imaging apparatus to the computer 107, a sample image can be confirmed on a computer screen. This imaging apparatus 108 corresponds to image input means 6 of FIG. 1, and a memory within the computer 107 to first storage means 7 of FIG. 1.

Figure 4:
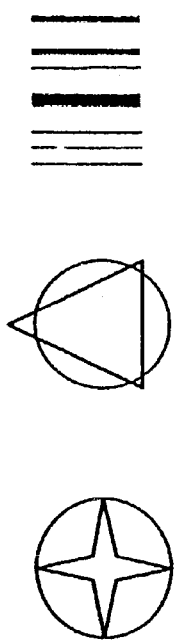
FIG. 4 is a figure showing an example of a figure depicted on the ID key of the embodiment of the invention.
Figure 3:
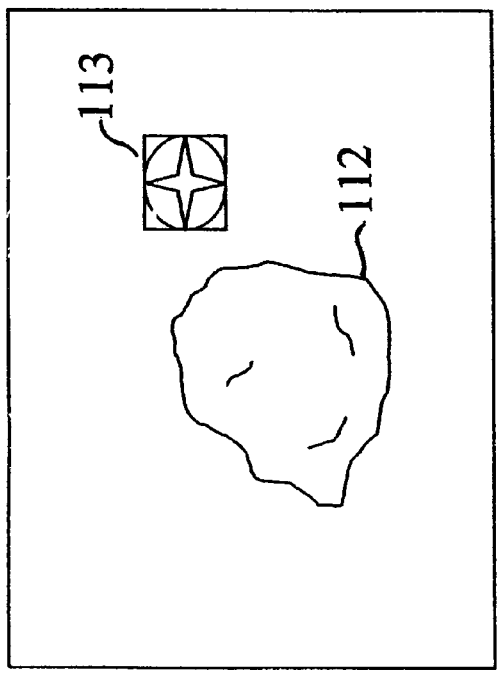
FIG. 3 is a figure showing a state the sample to be measured and ID key of the embodiment of the invention are image-inputted.

Measurement start, or start of radiation of X-rays to the sample to be measured, in this embodiment is ordered by the computer 107. An instruction signal for such measurement start is inputted to a shutter control circuit 110 by way of a signal line 109. The computer 107 and the signal line 109 constitute measurement start ordering means 5 of FIG. 1. In the usual fluorescent X-ray analyzer, a certain safety mechanism is provided so as not to cause exposure of X-rays to the measurer. That is, the state of a measuring head possessing an X-ray radiation function is measured to determine whether to radiate X-rays or not. Apparatus safety is secured if, for example, in the period of time when preparation is being made for X-ray radiation the measurer presses an X-ray radiation permission switch provided on the measuring head, or else, some structure is provided to depress the above X-ray radiation permission switch when the measuring head is attached to a specific position stabilizing base. Particularly, for a portable-type fluorescent X-ray analyzer, such safety mechanisms have to be provided at a plurality of positions to enhance safety, to maintain the characteristic that the measuring head is high in installation freedom. In the present embodiment, there is an X-ray radiation permission switch 111 as a first safety mechanism. The state of the X-ray radiation permission switch 111 is inputted to the shutter control circuit 110, this input treated subsequently as one condition for determining the shutter opening and closing operation. The X-ray radiation permission switch 111 corresponds to state detecting means 10 of FIG. 1, and the shutter control circuit 110 to X-ray switch means 11 of FIG. 1. A second safety mechanism utilizes the imaging apparatus 108 when the shutter control circuit 110 changes its determination whether or not data corresponding to a specified figure is contained in the data image-inputted simultaneously with that of the sample to be measured. An object whose shape specifications has been recorded is placed in a vicinity of the point to be measured. The object is of a size such that the shape thereof can be sufficiently easily recognized, e.g. it can be considered as a card-like object or where there is no trouble caused by sticking things on the sample to be measured, a seal-like one. An object to be image-recognized by the imaging apparatus 108 simultaneously with the sample to be measured is hereinafter referred to as an ID key. FIG. 3 shows a state that the sample to be measured 112 and the ID key 113 are image-inputted by the imaging apparatus 108. The figure recorded as the ID key may be in any form provided it is not readily confused with an object existing in nature. Should an extremely simple figure, such as a "circle" or "single straight line" be adopted as an ID key figure, there arises a fear that a "stone" or a "piece of a rod" be recognized as an ID key. Accordingly, a certain degree of uniqueness in the figure is required. However, complexity is desirably held at a minimum. This is because, in order to operate the safety mechanism more effectively, image recognition is preferably repeated as frequently as possible during measurement. For this, it is important to make the figure of the ID key as clear and simple as possible for reducing the burden in image analyzing processing. FIG. 4 shows examples of a figure of the ID key. Among these, a bar-code shown to the right is very practical.

A figure of the ID key is entered in the memory 107 of the computer. The memory part storing data related to an ID key figure corresponds to second storage means 8 of FIG. 1. As stated before, the memory of the computer 107 also stores image data acquired through the imaging apparatus 108, forming a part corresponding to the first storage means 7 of FIG. 1. Verification is made utilizing related data stored in the second storage means 8 to determine whether or not a figure identical to or corresponding to the ID key figure is included in data obtained through subjecting the content stored in the first storage means 7 to image processing such as filtering, binarizing or contour rendering. Where a figure corresponding to ID key figure data is found in the image data acquired as a result of data retrieval by the imaging apparatus 108, a signal notifying the fact is outputted from the computer 107. This signal is inputted to the shutter control circuit 110 by way of the signal line 114. The image processing and data retrieval utilizing the computer 107 and the function of delivering a signal upon finding a figure corresponding to the ID key figure data as above are represented as data comparing means 9 in FIG. 1.

The shutter control circuit 110 is input with a measurement start order signal, signals giving the state of the X-ray radiation permission switch 111 and a result of the search for a figure corresponding to the ID key figure data. The shutter control circuit 110 then executes control of driving the actuator 104 and opening the shutter 101 only where the conditions are satisfied that "there is a measurement start order", "the X-ray radiation permission switch 111 is in its permission state" and "A figure corresponding to the ID key figure data is found".

Figure 5:
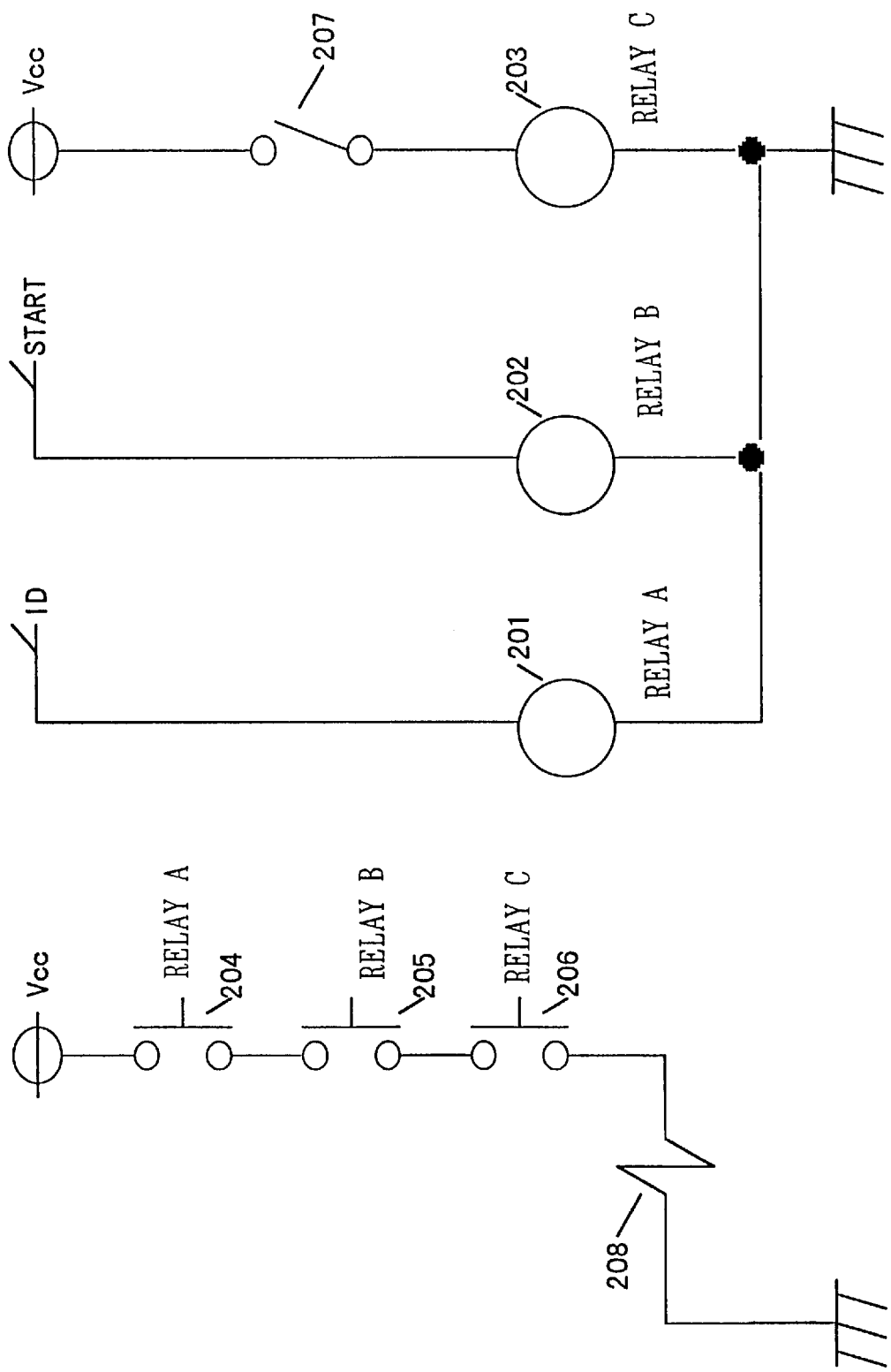
FIG. 5 is a configuration diagram of a shutter control circuit of the embodiment of the invention.

FIG. 5 shows an example of configuring a shutter control circuit 110. In a state that a figure corresponding to the ID key figure data is found, a current flows through a coil of a relay A201 due to a signal through the signal line 114, closing a contact 204. A measurement start instruction causes to flow through the signal line 109 a current through a coil of a relay B202, closing a contact 205. If an X-ray radiation permission switch 207 closes to indicate a permission state, a current flows through a coil of a relay C203, closing a contact 206. When in a state where simultaneously the three relay contacts are closed, a current flows through a solenoid 208. As a result, the excited solenoid 208 operates to open the shutter 101.

The present invention is structured such that, in a fluorescent X-ray analyzer, an ID key identified with a particular figure is put in the vicinity of a sample to be measured and previously read by the image input means, and the shutter drive means is controlled to open the shutter only where the conditions that the current figure image data is contained in the stored image data when a measurement start is instructed and that the signal from the state detecting means is an activation signal. This structure has the following effects.

(1) Because high safety is secured by the shutter operation control mechanism utilizing an ID key, the means for detecting an apparatus installation state as another safety mechanism may be simplified. Accordingly, the portable fluorescent X-ray analyzer is simplified in handling without hindrance to freedom in installing same.

(2) Because examination is made during measurement whether an ID key exists in an observation image or not, should this condition be unsatisfied, the shutter is closed to prohibit an X-ray from radiating to an outside. Accordingly, even if an accident occurs, e.g. the measuring head is blasted by a strong wind and changed in installation state during measurement or in X-ray radiation, the apparatus conducts fail-safe operations, thus securing safety.

(3) Because only a person possessing a particular ID key can perform measurement operation, there is no possibility that a third person contacts the apparatus to cause an exposure accident. Thus, safety is secured.

What is claimed is:

1. A fluorescent X-ray analyzer comprising: X-ray generating means for generating X-rays; a shutter for shielding an X-ray flux generated from the X-ray generating means from irradiating a sample to be measured; shutter drive means for opening and closing the shutter; X-ray detecting means for detecting secondary X-rays generated when the X-ray flux is radiated to the sample to be measured; measurement start order means for ordering the start of a measurement; image input means for optically reading and obtaining image data corresponding to an external appearance and a background of the sample to be measured; first storage means for storing image data obtained by the image input means; second storage means for storing data related to a figure previously registered; data comparing means for comparing the image data stored in the first storage means with the data stored in the second storage means; and state detecting means for detecting an installation state of the fluorescent X-ray analyzer.

2. A fluorescent X-ray analyzer according to claim 1; further comprising X-ray switch means for controlling the shutter drive means in accordance with outputs from the data comparing means and the state detecting means when a measurement start order is ordered by the measurement start order means.

3. A fluorescent X-ray analyzer according to claim 1; wherein the shutter drive means comprises an actuator.

4. A fluorescent X-ray analyzer according to claim 1; wherein the X-ray detecting means comprises one of a semiconductor detector, a scintillation detector and a proportional counter tube.

5. A fluorescent X-ray analyzer comprising: an X-ray radiating device for radiating a sample with X-rays; a shutter for undergoing opening and closing operations to control radiation of the sample by the X-ray radiating device; an imaging device for optically reading the sample and generating first image data corresponding to an image of the sample; a first storage circuit for storing the first image data; a second storage circuit for storing second image data corresponding to a preselected image; comparing means for comparing the first image data to the second image data; and control means for controlling the opening and closing operation of the shutter in accordance with a comparison result from the comparing means.

6. A fluorescent X-ray analyzer according to claim 5; wherein the control means comprises shutter drive means for driving the shutter to open and close, and switching means for controlling the shutter drive means to open and close the shutter.

7. A fluorescent X-ray analyzer according to claim 6; wherein the comparing means includes means for determining whether or not the first image data corresponds to the second image data; and wherein the switching means controls the shutter drive means to open the shutter when the comparing means determines that the first image data corresponds to the second image data.

8. A fluorescent X-ray analyzer according to claim 6; wherein the shutter drive means comprises an actuator.

9. A fluorescent X-ray analyzer according to claim 8; wherein the actuator comprises a solenoid.

10. A fluorescent X-ray analyzer according to claim 5; wherein the comparing means includes means for determining whether or not the first image data corresponds to the second image data; and wherein the control means includes means for controlling the shutter to open when the comparing means determines that the first image data corresponds to the second image data.

11. A fluorescent X-ray analyzer according to claim 5; wherein the imaging device comprises a CCD camera.

12. A fluorescent X-ray analyzer according to claim 5; further comprising detecting means for detecting secondary X-rays generated during radiation of the sample by the X-ray radiating device.

* * * * *